United States Patent
Alexander et al.

(10) Patent No.: US 9,956,066 B2
(45) Date of Patent: May 1, 2018

(54) VAGINAL DILATOR/MANIPULATOR

(71) Applicant: Boston Scientific Scimed, Inc., Maple Grove, MN (US)

(72) Inventors: James A. Alexander, Excelsior, MN (US); Micah D. Thorson, North Branch, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 213 days.

(21) Appl. No.: 14/776,067

(22) PCT Filed: Mar. 7, 2014

(86) PCT No.: PCT/US2014/021654
§ 371 (c)(1),
(2) Date: Sep. 14, 2015

(87) PCT Pub. No.: WO2014/149965
PCT Pub. Date: Sep. 25, 2014

(65) Prior Publication Data
US 2016/0022400 A1    Jan. 28, 2016

Related U.S. Application Data

(60) Provisional application No. 61/791,140, filed on Mar. 15, 2013.

(51) Int. Cl.
| | | |
|---|---|---|
| *A61F 2/00* | (2006.01) | |
| *A61B 1/32* | (2006.01) | |
| *A61B 1/06* | (2006.01) | |
| *A61B 17/02* | (2006.01) | |
| *A61B 1/303* | (2006.01) | |
| *A61M 29/00* | (2006.01) | |
| *A61B 17/00* | (2006.01) | |

(52) U.S. Cl.
CPC ............ *A61F 2/0009* (2013.01); *A61B 1/06* (2013.01); *A61B 1/32* (2013.01); *A61B 17/0218* (2013.01); *A61F 2/0063* (2013.01); *A61B 1/303* (2013.01); *A61B 2017/00907* (2013.01); *A61F 2002/0072* (2013.01); *A61M 29/00* (2013.01)

(58) Field of Classification Search
CPC ......... A61F 2/0045; A61B 2017/00805; A61B 90/02
See application file for complete search history.

(56) References Cited

U.S. PATENT DOCUMENTS

| | | |
|---|---|---|
| 2007/0230167 A1 | 10/2007 | McMahon et al. |
| 2010/0174132 A1* | 7/2010 | Gellman .......... A61B 17/00234 600/30 |
| 2010/0331622 A2 | 12/2010 | Conlon |

FOREIGN PATENT DOCUMENTS

| | | |
|---|---|---|
| WO | 2006/045042 A1 | 4/2006 |
| WO | 2006059321 A2 | 6/2006 |
| WO | 2007149348 A2 | 12/2007 |
| WO | 2012050973 A1 | 4/2012 |

* cited by examiner

*Primary Examiner* — Christine H Matthews
(74) *Attorney, Agent, or Firm* — Brake Hughes Bellermann LLP

(57) ABSTRACT

A dilator/manipulator for use in treating pelvic organ prolapse, including a support member having a proximal end, a distal end, and an adjustable width, and a handle extending upwardly at an angle from the support member. Also included are methods for surgically correcting pelvic organ prolapse with the use of such a dilator/manipulator.

18 Claims, 2 Drawing Sheets

VAGINAL DILATOR/MANIPULATOR

PRIORITY CLAIM

This application claims priority to International Application No. PCT/US2014/021654, filed Mar. 7, 2014, which in turn claims the benefit of U.S. Provisional Patent Application No. 61/791,140, filed Mar. 15, 2013 and titled Vaginal Dilator/Manipulator, the disclosures of which are incorporated herein by reference in their entireties.

TECHNICAL FIELD

The present invention relates to systems, tools, and methods for treating pelvic organ prolapse by use of a pelvic implant to support pelvic tissue. The pelvic treatments include, for example, treatment of vaginal prolapse by laparoscopic or abdominal procedures.

BACKGROUND

Pelvic health for women is a medical area of increasing importance, at least in part due to an aging population. Examples of common pelvic ailments include incontinence (e.g., fecal and urinary incontinence), pelvic tissue prolapse (e.g., female vaginal prolapse), and other conditions that affect the pelvic floor. Pelvic disorders such as these can be caused by weakness or damage to normal pelvic support systems. Common etiologies include childbearing, removal of the uterus, connective tissue defects, prolonged heavy physical labor, and postmenopausal atrophy.

Pelvic floor disorders include cystocele, rectocele, and prolapse such as anal, uterine, and pelvic organ prolapse. Pelvic organ prolapse is a condition that occurs when the upper portion of the vagina loses its normal shape and moves downwardly into the vaginal canal. In its severest forms, pelvic organ prolapse can result in the distension of the vaginal apex outside of the vagina. Pelvic organ prolapse may occur alone, such as can be caused by weakness of the pelvic and vaginal tissues and muscles, or can be associated with a rectocele, cystocele and/or enterocele. Prolapse can represent a challenge for surgeons to treat. Some of these treatments include, for example, abdominal sacralcolpopexy (SCP), which may be performed laparoscopically, and transvaginal sacral colpopexy (TSCP), wherein these procedures are performed using a variety of different instruments, implants, and surgical methods. It is known to repair pelvic organ prolapse by suturing the vaginal vault (e.g., by stitches) to the supraspinous ligament or by attaching the vaginal vault through mesh or fascia to the sacrum. In addition, doctors are currently using devices such as an EA sizer or other device when performing an SCP procedure, which devices are acceptable for many applications. However, presently available devices have surgical limitations in certain situations that present opportunities for improvements and enhancements.

Thus, there is ongoing need to provide physicians with improved methods and associated systems, tools, and implants for treating pelvic conditions such as pelvic organ prolapse, wherein such methods can include those that are minimally invasive, safe, and highly effective.

SUMMARY

Systems, tools, and methods as described herein can be used to treat pelvic conditions such as vaginal prolapse caused by muscle and ligament weakness, hysterectomies, and the like. In accordance with the invention, sacral colpopexy procedures can be performed through an abdominal opening, laparoscopically, or transvaginally, each of which may require different approaches, which can use certain embodiments of systems and/or methods of the invention.

In a sacral colpopexy procedure it is desirable to simplify the process of attaching an implant within a patient using implantation tools and fasteners having various features. Implants can include those that are Y-shaped, which include a base member and two support members extending from the base member, wherein the attachment of portions of the Y-shaped implant can be adjustable relative to their respective attachment points within a patient (e.g., the sacrum). Additionally, a Y-shaped implant can include at least two pieces (an extension portion or a support portion) that engage with each other. Systems described herein relate to systems and methods to aid in implantation of a pelvic implant, such as a Y-sling.

Certain embodiments of methods and implants described herein involve the use of a Y-shaped sling that is designed to fixate to the sacral promontory, and may additionally include two apical mesh pieces that are sutured to the anterior and posterior vaginal walls. Embodiments of implants and methods can involve placement of an implant to support pelvic tissue, by way of an incision of minimum size.

Certain embodiments relate generally to fixation of the Y-shaped sling and related means for fixing the pelvic implant to the vagina for the treating of pelvic organ prolapse. Embodiments of the system can include an implant having a tissue support portion and one or more extension portions, fasteners, and a dilator. Devices of the invention, which may be referred to as a vaginal dilator/manipulator, can be expandable to fit differently sized vaginas. The devices may include the use of a sheath temporarily positioned to surround at least a portion of the outside of the device to prevent "pinching" during manipulation, and/or which maintains the device in its most compact form.

Devices of the invention operate by pushing a handle of the device into the vagina, which can cause the device to expand to fill the vagina and hold the anterior and posterior aspects flat. The device can include an elongated U-shaped member attached to a light source to illuminate the vagina, which can help to provide feedback regarding the tissue thickness and help in the dissection process. The device can include long and flat anterior and posterior pieces that provide for suture depth feedback in order to allow a physician to better control partial or full thickness suture passes.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
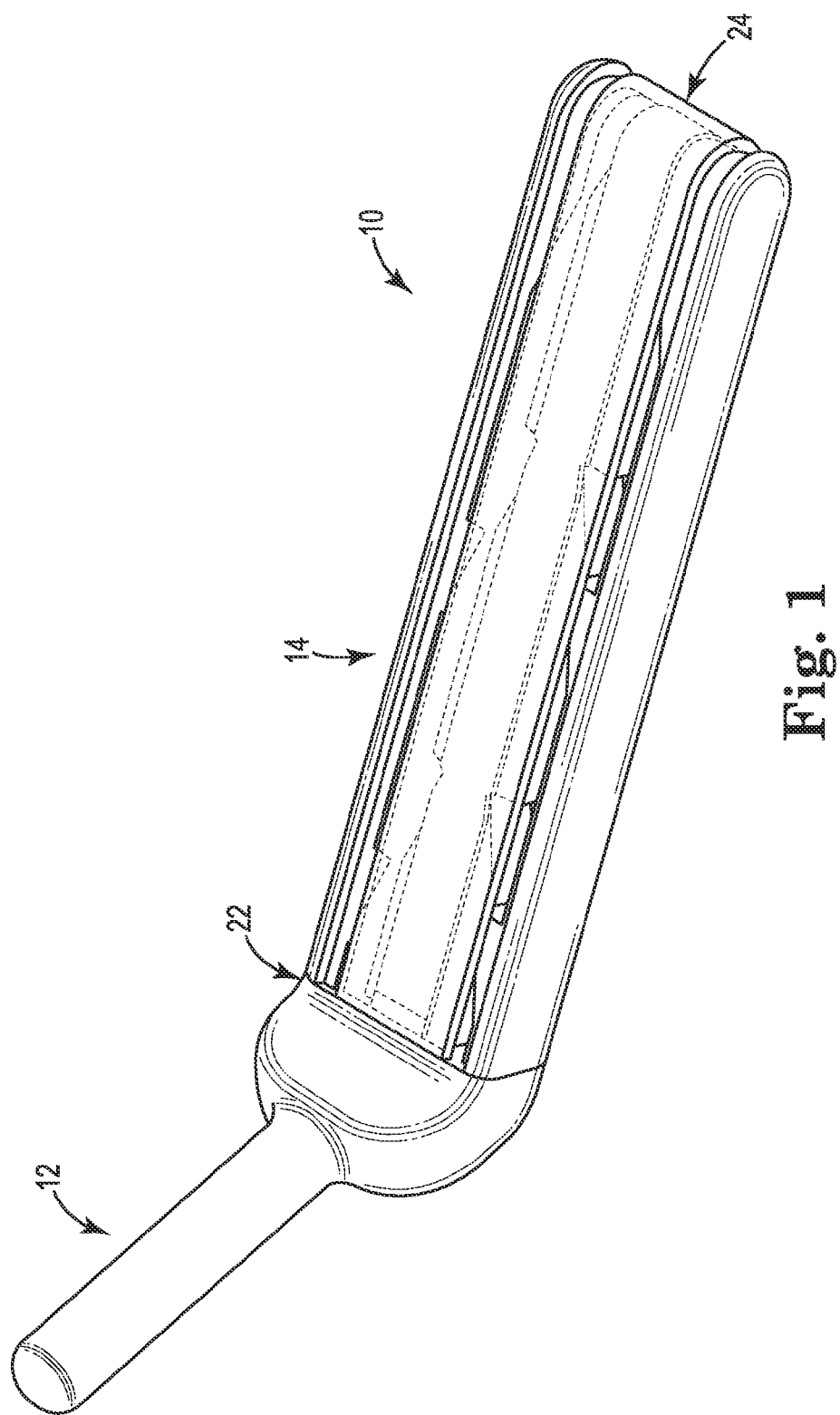
FIG. 1 is a perspective view of a vaginal dilator/manipulator in a compact state, in accordance with the invention.

The methods and tools as described can be useful in procedures for supporting vaginal tissue, such as methods to treat pelvic organ prolapse by a sacral colpopexy procedures. A sacral colpopexy is a procedure for providing vaginal vault suspension, which can be accomplished with the use of an implant such as a strip of mesh or other material of posterior vaginal tissue (e.g., a vaginal cuff) to a region or component of sacral anatomy such as the sacrum (bone itself), a nearby sacrospinous ligament, uterosacral ligament, or anterior longitudinal ligament at the sacral promontory, such as may be accomplished using bone screws that are implanted into the sacrum. Sacral colpopexy may be performed through an abdominal incision or laparoscopically. In some sacral colpopexy procedures that also involve a hysterectomy, an implant can alternatively be attached to posterior vaginal tissue that remains after removal of the uterus and cervix, and also to anatomy to support the vaginal tissue at or around the sacrum, such as to uterosacral ligaments or to the sacrum itself (i.e., to a component of the sacral anatomy). Implants for these procedures are known, as described and illustrated at Assignee's co-pending provisional patent application having U.S. Ser. No. 60/583,146, filed on Jun. 25, 2004, by Bouchier et al., entitled POLYMER ATTACHMENT METHOD FOR IMPLANTABLE ARTICLES, IMPLANTABLE ARTICLES, AND METHODS, the entirety of which is incorporated herein by reference.

Implants as described may be of a type that is useful as a surgical implant to support tissue in a method of addressing and treating a condition of pelvic tissue, such as to address a pelvic floor disorder such as prolapse (e.g. vaginal, such as vaginal vault prolapse), enterocele (e.g. of the uterus), rectocele, and cystocele. Non-urological procedures such as eventration or hernia repair, and visceral, parietal, and neurological procedures, are also contemplated applications. In an exemplary embodiment, a vaginal dilator/manipulator is used in a sacral colpopexy procedure. It is contemplated that the implant may also be useful in conjunction with other procedures such as but not limited to culposuspension, culdoplasty, procedures for addressing cystocele prolapse, and other surgical procedures that use an implant. Examples of implants that include features in common with implants of the present description are shown and described in Assignee's co-pending application having U.S. Publication No. 2012/0022318, filed Oct. 4, 2011, by Thierfelder et al., entitled IMPLANTABLE ARTICLE AND METHOD, the entirety of which is incorporated herein by reference.

The devices and methods as described herein can be useful in procedures for placement of a pelvic implant for a sacral colpopexy procedure. Exemplary procedures include laparoscopic or abdominal sacral colpopexy procedures. An exemplary laparoscopic sacral colpopexy procedure includes introducing the implant (i.e., a Y-sling) into the abdomen and using a fastening mechanism to attach the implant to the vaginal cuff. A dilator may aid in locating the vaginal cuff during such procedure.

The devices of the present invention are generally referred to herein as vaginal dilator/manipulators. These devices are provided to support vaginal tissue internally while laparoscopic surgery is being performed in the vaginal area. That is, the device is inserted into the patient so that the surgeon can manipulate post-vaginal tissue while operating laparoscopically. This device can be disposable or reusable, and is structured to reduce surgical time and improve surgical outcomes by aiding in tissue dissection and suture/mesh placement. The device can be made using an inexpensive acrylonitrile butadiene styrene (ABS) or polycarbonate material that comprises effective light conduction properties.

Figure 2:
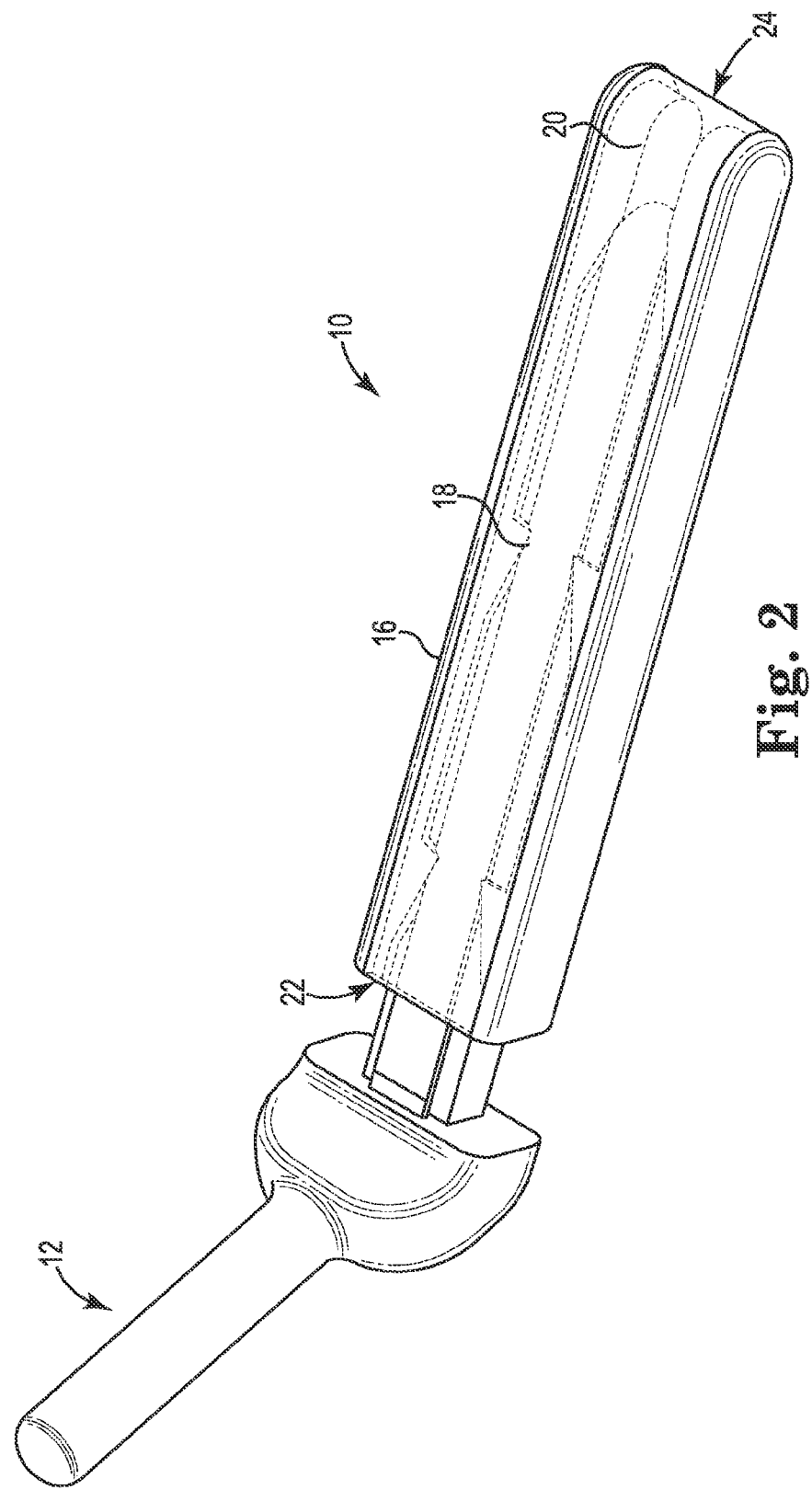
FIG. 2 is a perspective view of the vaginal dilator/manipulator of FIG. 1, shown in its partially expanded state.

Referring now to FIGS. 1 and 2, wherein the components are labeled with like numerals throughout the Figures, one configuration of a vaginal dilator/manipulator 10 of the invention is illustrated. The dilator/manipulator 10 is shown in its compact state in FIG. 1, and in a partially expanded state in FIG. 2. With this configuration, the dilator/manipulator 10 can be changed in size during use to accommodate different anatomies and/or various manipulations that are desired during the surgical procedure. Because the dilator/manipulator 10 is provided with minimal seams or pinch points, the risk of tissue being pinched and/or damaged while using this device is low.

The dilator/manipulator 10 includes a handle 12 that extends from a support member 14. The support member 14 includes an outer frame 16 and an inner slide member 18 that is slidable relative to the width of outer frame 16. In particular, outer frame 16 includes an inner slot 20 that extends along its width from its proximal end 22 to its distal end 24. The inner slot 20 can be generally smooth along its length or can include one or more protrusions that are configured for selective engagement with the slide member 18. In this embodiment, the thickness of the dilator/manipulator 10 is constant, but the width is variable. Twisting or otherwise manipulating the handle 12 can be used to change the width of the dilator/manipulator 10, when desired, or the width change can be performed by simply pushing or pulling the slide member 18 relative to the slot 20. When the slide member 18 extends even slightly from the slot 20, the dilator/manipulator is considered to be larger in the width dimension than when it is fully inserted in the slot 20.

In an embodiment of the invention, the handle 12 is positioned at an angle of approximately 30 degrees relative to the plane of the top surface of the support member 14. When in use, the handle 12 will be angled away from the operating table, thereby avoiding interference between the handle 12 and the operating table during the surgical procedure. That is, the angle of the handle 12 relative to the support member 14 can allow for articulation of the vaginal canal without interference between the handle 12 and the table. Therefore, it is understood that this angle can be greater or less than 30 degrees, wherein the angle is chosen to provide the easiest access for the surgeon without undue reorientation of the device during the surgical procedure.

A flat surface of the support member 14 can provide a surface that is useful as a "backstop" for a surgeon that is suturing during the surgical procedure. In one exemplary procedure, the suturing process can involve penetrating multiple layers of material with a needle (e.g., one or more tissue layers and an implant layer, multiple tissue layers, etc.), where one of the layers is directly in contact with a flat surface of the support member 14 of the dilator/manipulator 10. The suturing process can include extending the suture through all or some of the layers, wherein the support member 14 can provide a gauge for the surgeon to feel where the outer layer of material is located, and/or can be used as a physical barrier to prevent the surgeon from unintentionally penetrating tissue or organs beyond the layers that are intended to be sutured. That is, support member 14 can include long and flat anterior and posterior pieces that provide for suture depth feedback in order to allow a physician to better control partial or full thickness suture passes.

The dilator/manipulator 10 can further be provided with a device or structure that provides illumination. Such illumination can be provided by making portions of the dilator/manipulator 10 from a translucent material that emits light in predefined areas, and/or by providing protrusions through which light can be emitted and/or by other manners of light emission. It is further contemplated that illumination can be provided by a laparoscopic light or other light source fed through the dilator/manipulator, such as can be provided by a fiber running along at least a portion of the length of the support member 14 and/or handle 12.

The dilator manipulator 10 may include the use of a sheath (not shown), that is positioned to temporarily surround at least a portion of the outside of the device to prevent "pinching" during manipulation thereof. Such a sheath can also be used to keep the device in its most compact form, wherein the slide member 18 is fully inserted into the slot 20.

In one embodiment, a Y-sling is placed over the vaginal cuff and suspended up in the peritoneal cavity and the vaginal dilator/manipulator 10 is inserted into the vagina.

An implant for placement by use of the described systems, tools, and methods, and their various components, structures, features, materials and methods may have a number of suitable configurations as shown and described in the previously-incorporated references or as described herein or elsewhere. Various methods and tools for introducing, deploying, anchoring, and manipulating implants to treat prolapse, as disclosed in the previously-incorporated references are envisioned for possible adapted use with devices and methods described herein.

An implant for use as described herein can include any structural features useful for a desired treatment, including any desired size, shape, and optional features such as adjustability. Any of these features may be previously known, or described in documents incorporated herein, or as described herein, for any particular implant and method. An implant that includes or is otherwise secured, adjusted, and manipulated as described might be useful to treat pelvic organ prolapse in a transvaginal sacral colpopexy procedure to provide support to vaginal tissue (e.g. a vaginal cuff), through an implant attached at a region of sacral anatomy such as a sacral ligament (e.g., anterior longitudinal ligament)

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A medical device for use in treating pelvic organ prolapse, comprising:
   a support member including a distal end and a proximal end, the support member including an outer member, the outer member having a first surface and a second surface opposite to the first surface, the outer member having an open end and a closed end, the outer member defining a slot at the open end and extending into the outer member along at least a portion of a length of the outer member between the first surface and the second surface, the support member including an inner member at least partially disposed within the slot of the outer member; and
   a handle fixedly coupled to the inner member, the handle having a portion extending upwardly at an angle from the support member, the inner member configured to slide relative to the outer member to adjust a distance between the distal end and the proximal end,
   wherein the inner member is configured to move from a first position in which the outer member at the open end contacts the handle and a second position in which the outer member at the open end is disposed a distance away from the handle.

2. The medical device of claim 1, wherein the pelvic organ prolapse comprises vaginal prolapse.

3. The medical device of claim 1, wherein the slot is smooth along at least a portion of the length of the outer member.

4. The medical device of claim 1, wherein the slot includes at least one protrusion for selective engagement with an outer surface of the inner member.

5. The medical device of claim 1, wherein the support member has a constant thickness along its length.

6. The medical device of claim 1, further comprising:
   a Y-shaped implant.

7. The medical device of claim 6, wherein the Y-shaped implant comprises at least one of a synthetic mesh, a biological graft, and another biocompatible material.

8. The medical device of claim 1, further comprising a light source.

9. The medical device of claim 8, wherein the support member includes a translucent material.

10. The medical device of claim 9, wherein the translucent material provides for light emission in at least one predetermined area.

11. The medical device of claim 8, further comprising at least one protrusion through which light from the light source is emittable.

12. The medical device of claim 1, wherein the first surface is flat.

13. A method of surgically correcting pelvic organ prolapse, the method comprising:
    inserting a medical device into a vagina of a patient, the medical device including a support member, the support member including a distal end and a proximal end, the support member including an outer member, the outer member having a first surface and a second surface opposite to the first surface, the outer member having an open end and a closed end, the outer member defining a slot at the open end and extending into the outer member along at least a portion of a length of the outer member between the first surface and the second surface, the support member including an inner member at least partially disposed within the slot of the outer member, the medical device including a handle fixedly coupled to the inner member;
    adjusting a distance between the distal end and the proximal end by sliding the inner member relative to the outer member;
    inserting a pelvic implant into an abdomen of the patient;
    attaching the pelvic implant to vaginal tissue of the patient; and
    removing the medical device from the vagina.

14. The method of claim 13, wherein the pelvic implant comprises a Y-shaped implant.

15. The method of claim 13, wherein the attaching the pelvic implant to the vaginal tissue includes suturing the pelvic implant to the vaginal tissue while using the support member to provide suture depth feedback.

16. The method of claim 13, wherein the handle has a portion extending upwardly at an angle from the support member.

17. The method of claim 13, wherein the adjusting includes moving the inner member from a first position in which the outer member at the open end contacts the handle to a second position in which the outer member at the open end is disposed a distance away from the handle.

18. The method of claim 13, wherein the first surface is flat.

* * * * *